(12) United States Patent
Rempt et al.

(10) Patent No.: US 7,375,514 B2
(45) Date of Patent: May 20, 2008

(54) FLEXIBLE HAND HELD MR SCANNING ARRAY FOR CRACKS/FLAWS

(75) Inventors: Raymond D. Rempt, Woodinville, WA (US); George A. Perry, Federal Way, WA (US)

(73) Assignee: The Boeing Company, Chicago, IL (US)

( * ) Notice: Subject to any disclaimer, the term of this patent is extended or adjusted under 35 U.S.C. 154(b) by 33 days.

(21) Appl. No.: 11/163,834

(22) Filed: Nov. 1, 2005

(65) Prior Publication Data

US 2007/0096727 A1  May 3, 2007

(51) Int. Cl.
*G01N 27/82* (2006.01)
(52) U.S. Cl. .................. 324/238; 324/235
(58) Field of Classification Search ............ 324/238, 324/225, 228, 235, 260–262
See application file for complete search history.

(56) References Cited

U.S. PATENT DOCUMENTS

| | | | | |
|---|---|---|---|---|
| 4,271,393 A | * | 6/1981 | Hansen et al. ............. | 324/240 |
| 5,841,277 A | * | 11/1998 | Hedengren et al. ........ | 324/240 |
| 6,150,809 A | * | 11/2000 | Tiernan et al. ............ | 324/238 |
| 2007/0100579 A1 | * | 5/2007 | Rempt et al. .............. | 702/168 |

\* cited by examiner

*Primary Examiner*—Reena Aurora
(74) *Attorney, Agent, or Firm*—Felix L. Fischer

(57) ABSTRACT

A non-destructive testing device has an excitation coil with a plurality of conductor ribbons attached to a flexible membrane. A frame supports the membrane and incorporates wheels for translation across a surface to be inspected and resilient suspension for maintaining the membrane with the excitation coil and wheels in intimate contact with the surface, the membrane flexing to maintain contact with a smoothly curved surface as found in aircraft structures. A magnetoresitive (MR) array is supported within the frame inserted in the membrane to be in close proximity to the surface. The MR array detects the magnetic field resulting from the eddy currents created by the excitation coil for identification of cracks or features beneath the surface under inspection.

17 Claims, 6 Drawing Sheets

FLEXIBLE HAND HELD MR SCANNING ARRAY FOR CRACKS/FLAWS

DEVELOPMENT UNDER GOVERNMENT CONTRACT

This invention was made with Government support under contract number N00014-04-C-0182 awarded by the United States Navy Office of Naval Research. The government has certain rights in this invention.

REFERENCE TO RELATED APPLICATIONS

This patent application is related to copending application Ser. No. 11/163,785 filed substantially concurrently herewith entitled "CONTROL FOR HAND-HELD IMAGING ARRAY USING COMPUTER MOUSE" having common inventors and a common assignee with the present application, the disclosure of which is incorporated herein by reference.

BACKGROUND OF THE INVENTION

1. Field of the Invention

This invention relates generally to the field of non-destructive inspection (NDI) of structures and more particularly to a Magnetoresistive (MR) scanning array employing flexible excitation coils incorporated in a hand held positioning device.

2. Description of the Related Art

Non-destructive inspection (NDI) of a aerospace structures to detect flaws may be performed by various techniques that include X-ray radiography, ultrasonics, acoustic emissions, and eddy currents. In particular, eddy current inspection devices are commonly used for NDI of electrically conductive components. Eddy current inspection devices typically use one or more excitation coils to generate an alternating magnetic field, which in turn induces eddy currents in the component, and typically use a pickup coil to detect the magnetic field generated by the eddy currents. When an eddy current encounters an internal flaw of the component, the eddy current flows around the flaw and the resulting magnetic field generated by the eddy current is changed. The pickup coil indirectly detects this change which gives information regarding the location and size of the flaw within the component.

Magnetoresistive (MR) sensors are known for low frequency performance permitting deep feature/flaw detection in metallic structure at sensitivities considerably above those provided by convention eddy current techniques. Exemplary NDI systems employing MR are disclosed in U.S. Patent No. 6,150,809 to Tiernan et al. which uses two parallel sheets of conductors to create the magnetic field and uses a giant magnetoresistive (GMR) sensor positioned between the sheets to detect the magnetic field signals generated by eddy currents and application Ser. No. 10/923,519 entitled EDDY CURRENT INSPECTION DEVICE, having a common assignee with the present invention, the disclosure of which is incorporated herein by reference.

Current imaging scanners using MR sensors are not flexible and therefore cannot conform to the surface of the item they are inspecting. In order to be able to faithfully display the subsurface condition of a complex structure such as an aircraft, in some cases it is therefore desirable that the scanner conform to the surface shape and curvature. This allows better coupling of the inspection current into the aircraft, and prevents erroneous scan results from the "rocking" motion of a non-flexible scanner on the curved aircraft surface. Additionally, it is desirable that the scanner be mounted in a structure for operation by hand to allow a technician to accurately yet conveniently perform inspection of the desired structure.

SUMMARY OF THE INVENTION

A system incorporating the present invention provides a non-destructive testing device having an excitation coil with a plurality of conductor ribbons attached to a flexible membrane. A frame supports the membrane and incorporates means for translation across a surface to be inspected and resilient means for maintaining the membrane with the excitation coil and the translation means in intimate contact with the surface. A magnetoresistive (MR) array is supported within the frame inserted in the membrane to be in close proximity to the surface. The MR array detects the magnetic fields resulting from eddy currents created by the excitation coil for identification of cracks in the surface under inspection.

Flexibility of the membrane and excitation coil allows inspection of curved surfaces not possible with rigid excitation devices. Placement of the MR array substantially perpendicular to the flexible excitation coil allows orientation of the array substantially perpendicular to the surface while remaining in close contact along the entire length of the array.

BRIEF DESCRIPTION OF THE DRAWINGS

These and other features and advantages of the present invention will be better understood by reference to the following detailed description when considered in connection with the accompanying drawings wherein.

DETAILED DESCRIPTION OF THE INVENTION

The present invention provides the capability to scan with an imaging array of MR sensors on curved surfaces, such as those commonly found on aircraft fuselages and wings. The excitation coil is flexible, and is attached to a piece of flexible material, such as a dense foam rubber. The density and flexibility of this material, to which the coil is affixed, ensures that the coil remains in intimate contact with the top surface of the component undergoing inspection. Downward pressure applied by the operator during the scanning ensures that this contact is continuous, and uninterrupted.

Figure 1A:
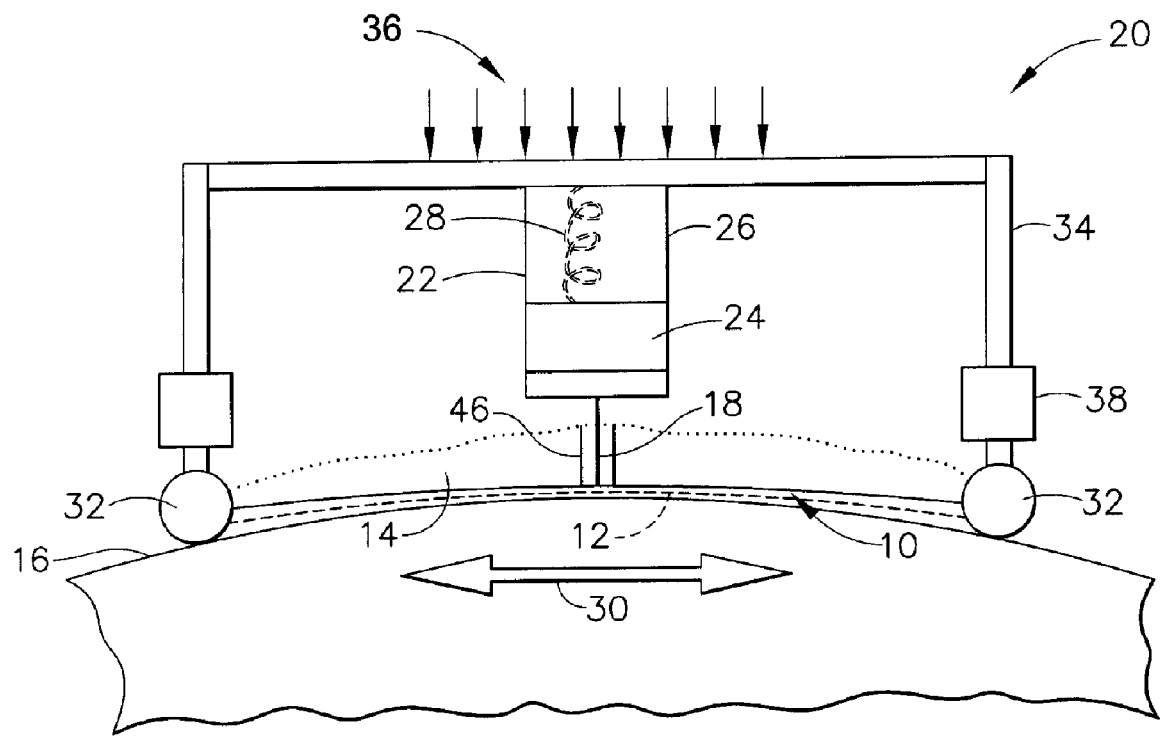
FIG. 1a is schematic diagram of the elements of the present invention in a circumferential scanning direction.
Figure 1B:
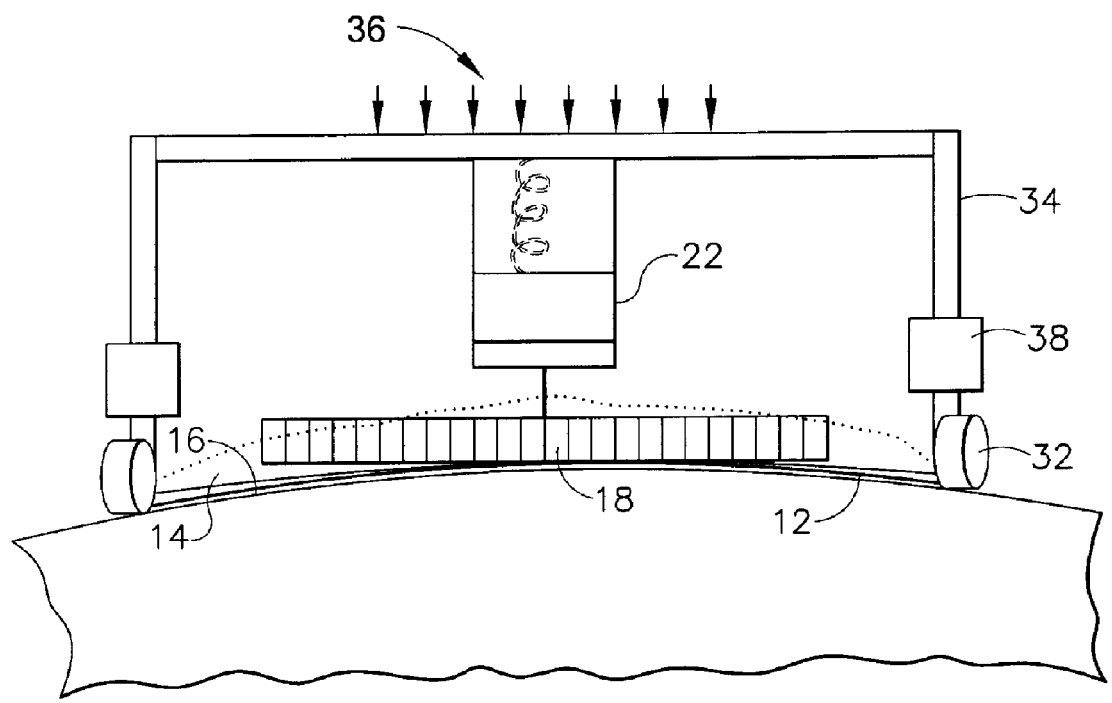
FIG. 1b is schematic diagram of the elements of the present invention in an axial scanning direction.

An embodiment of the invention is shown schematically in FIGS. 1a and 1b. A coil 10, with its conducting ribbons 12 perpendicular to the plane of the drawing in FIG. 1a and parallel to the plane of the drawing in FIG. 1b is shown in a gently curved configuration. The coil is embedded in or mounted on a flexible membrane or pad 14 of rubber or other nonconductive substrate. In an exemplary embodiment medium soft closed cell blended neoprene sponge identified by product number CCNS SCE 41 is employed as the membrane. The surface under inspection 16 is the shape which defines the curved shape of the coil through intimate contact between the coil and membrane and the surface.

Figure 3:
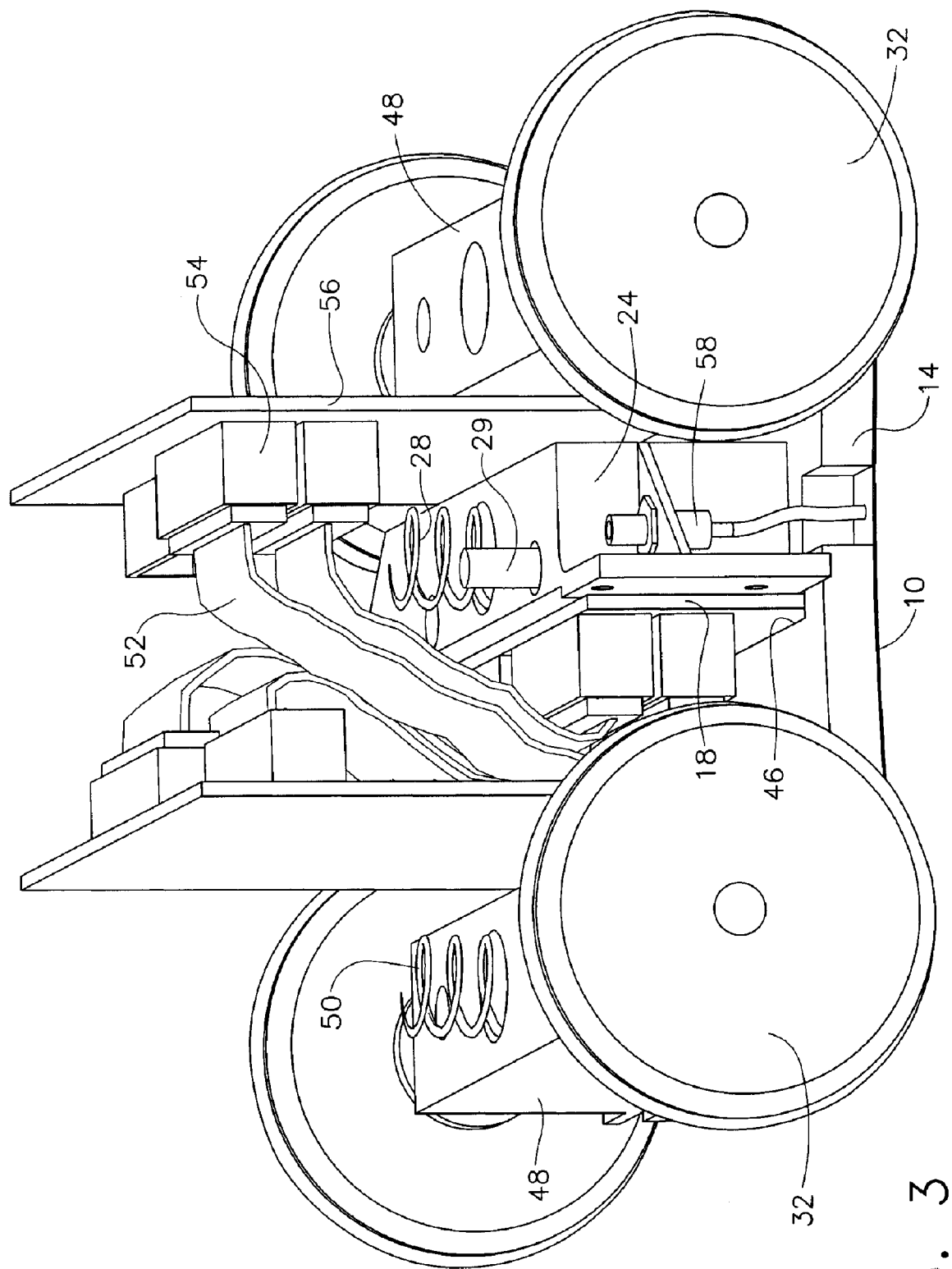
FIG. 3 is an isometric cutaway view of an embodiment of the invention showing structural details.
Figure 4:
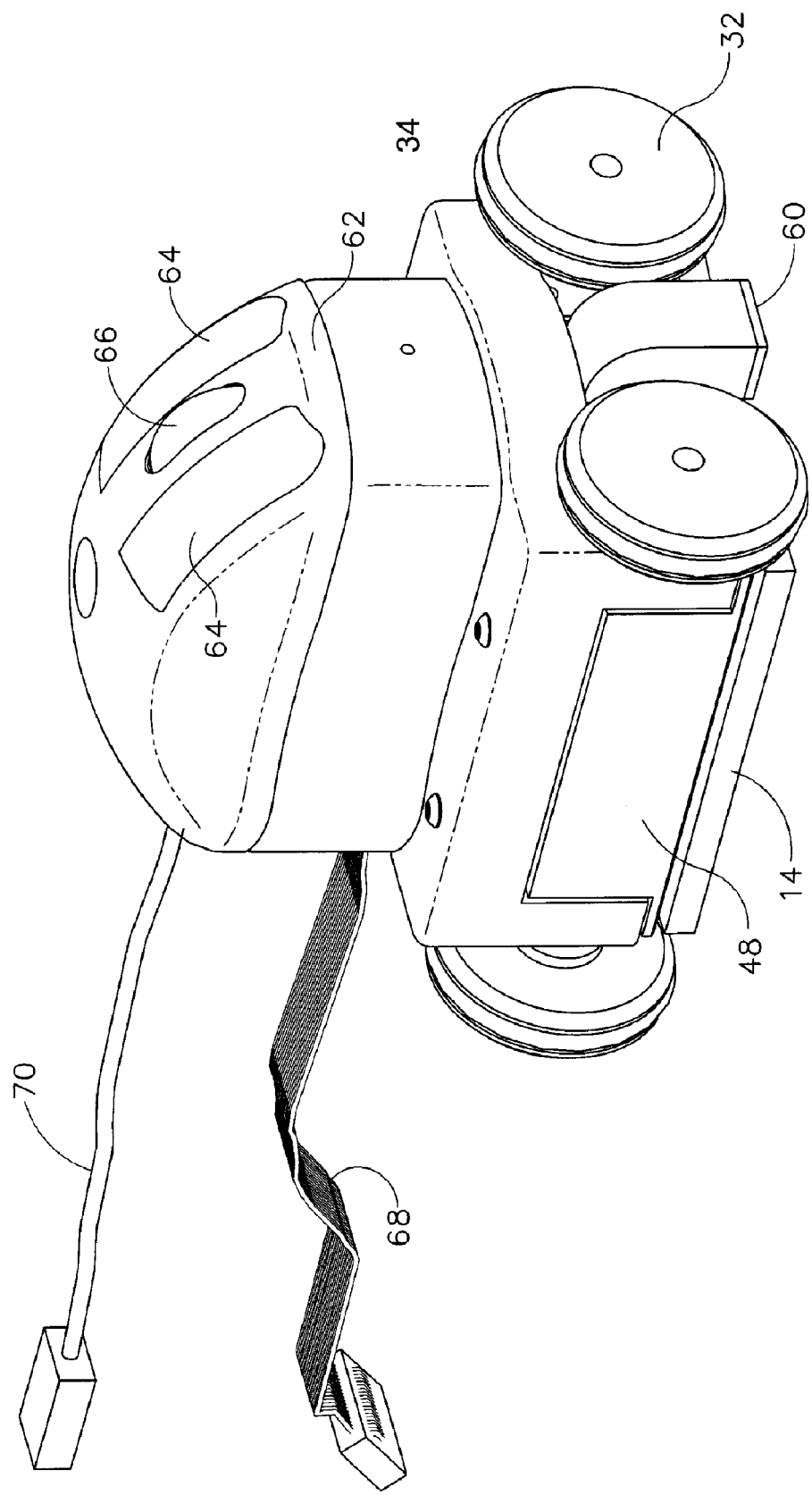
FIG. 4 is an isometric external view of the embodiment of FIG. 3.

A sensor array 18 is contained in a housing 20. This housing, described in greater detail with respect to FIGS. 3 and 4, is shaped ergonomically so that an inspector can easily cause it to glide across the surface of the aircraft being inspected. The array is supported by a resilient mount 22 shown as piston or block 24 constrained within a cylinder or channel 26 and loaded by a spring 28. For purposes of description herein, the scan motion is left and right in the configurations shown in FIG. 1a for circumferential scanning as represented by double arrow 30 at the bottom of the figure and perpendicular to the plane of the drawings in FIG. 1b for axial scanning, i.e. perpendicular to the circumferential direction of the curvature of the surface. Wheels 32 support the housing with respect to the surface under inspection and protrude coincident with or slightly beyond the coil, so that the coil is in contact with the surface as well as the wheels themselves. In exemplary embodiments the wheels employ a resilient material for contact with the surface to enhance the overall system contact.

A rigid frame 34 provides for transferring downward pressure exerted by the inspector, as represented by arrows 36, to maintain the intimate contact on the surface by the flexible coil and membrane. The frame incorporates resilient structural elements 38 providing spring loads, so that pressure is always applied when the inspector presses downward on the array head. The displacement range of the resilient elements allows for various radii of curvature in the surface of the item being inspected to be accommodated, while maintaining continuous and total contact between the surface being inspected and the excitation coil.

Figure 2A:
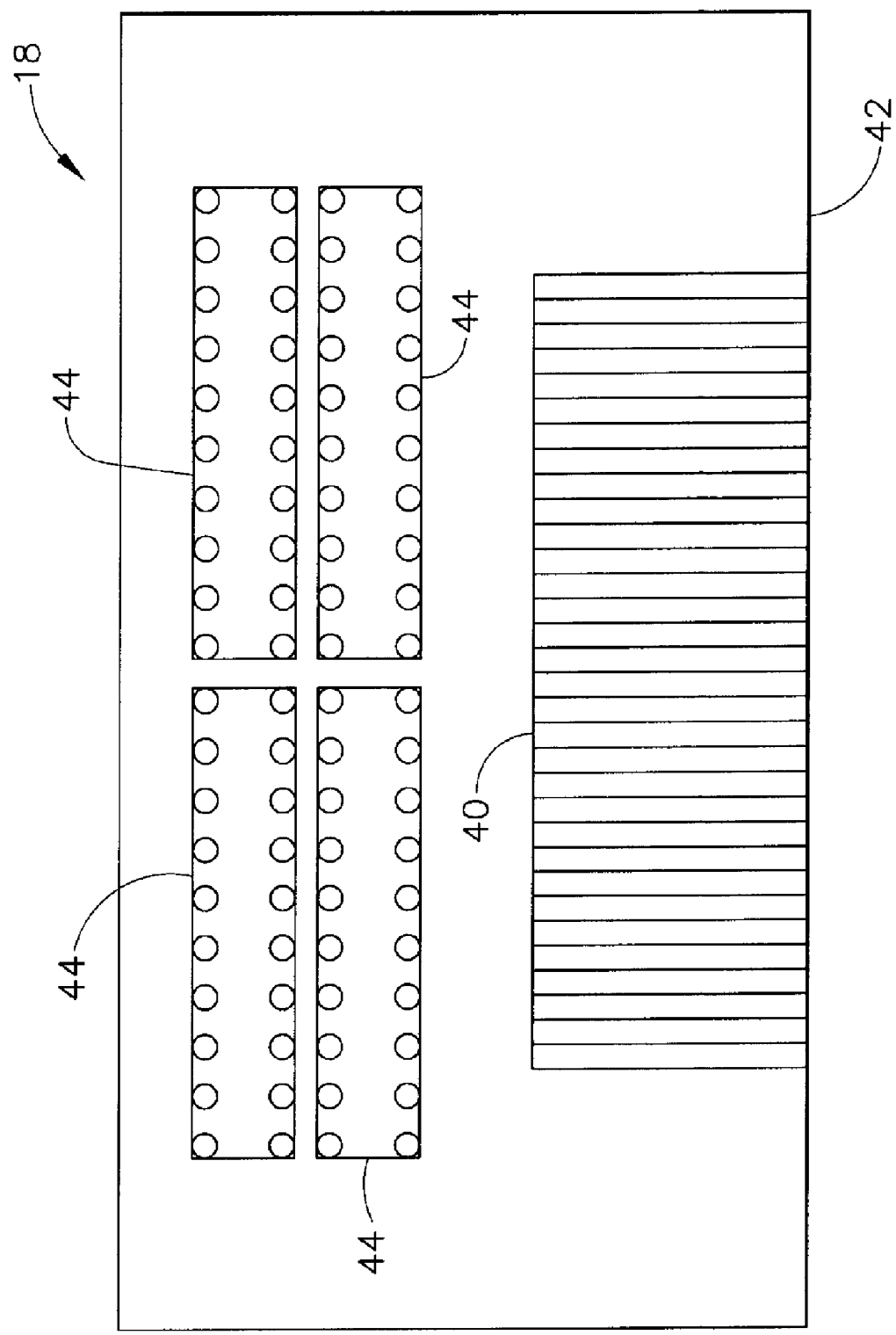
FIG. 2a is a diagram of the MR sensor array printed circuit board.

The scanning MR array is shown in FIG. 2a. For the embodiment disclosed, the array employs 32 elements 40 oriented along the lower edge of a printed circuit board 42. Multiple connectors 44 provide external connection to the elements through integral wiring on the PC board. Giant Magnetoresistive sensors (GMR) are employed in the embodiment disclosed. Inter-sensor spacings of 0.020 inch and 0.031 inch have been employed in exemplary devices employing the invention.

Figure 2B:
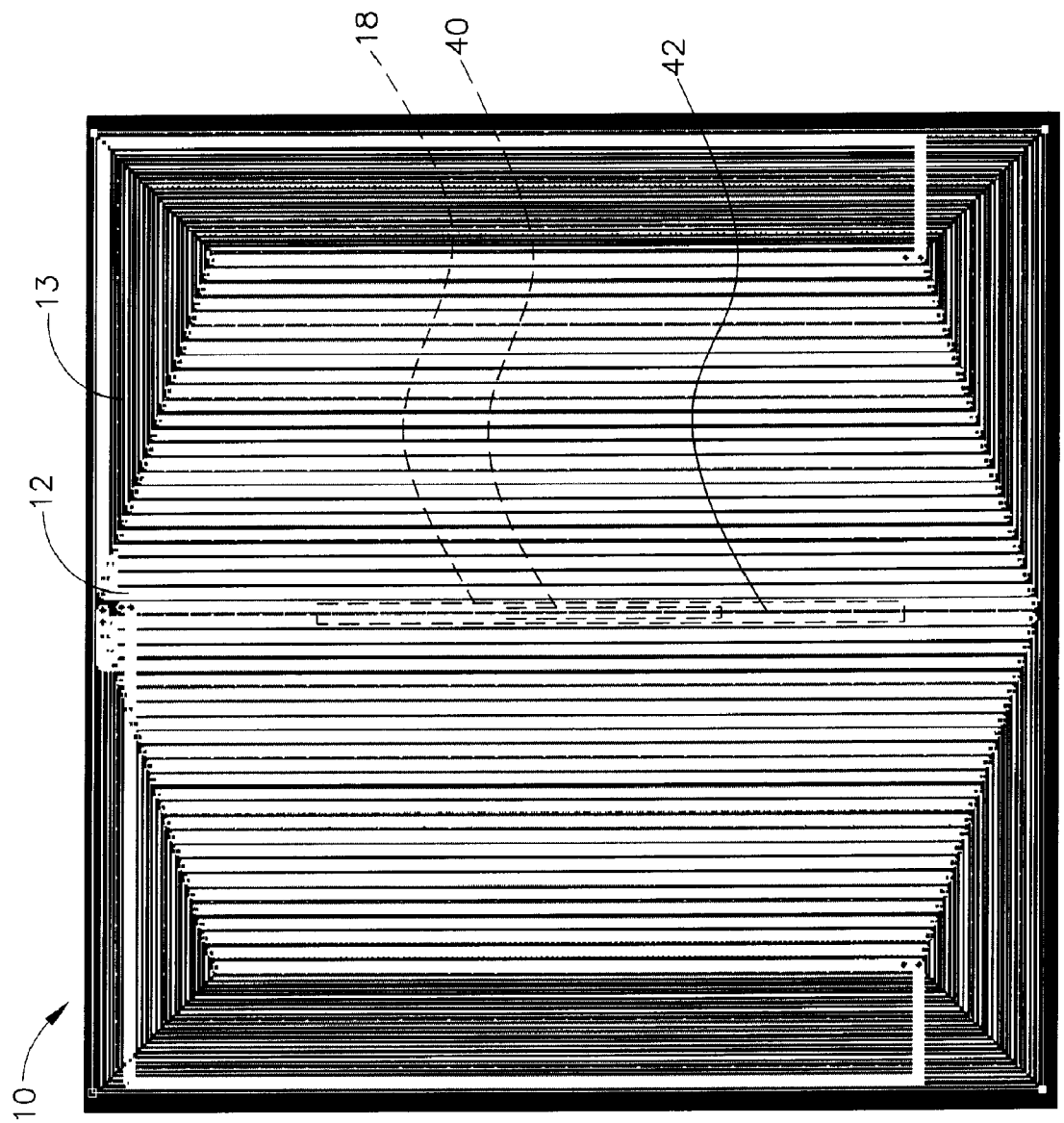
FIG. 2b is a mask of a printed circuit embodiment of the excitation coil.

FIG. 2b shows a printed circuit coil employed in an exemplary embodiment. Ribbons 12 are interconnected by traces 13 to create continuity in the coil. The small trace size and separation of the ribbons allows flexibility in the coil required for conformal adherence to the flexible membrane. The footprint created by sensors of array 18 and its mounting PC board are shown in phantom.

Alternative embodiments employ an isotropic magnetoresistive (AMR) sensors in staggered arrays and the invention disclosed herein is applicable for use with spin dependent tunneling (SDT) MR sensors for alternative inspection applications.

The PC board mounting the MR array is positioned perpendicular to the membrane mounted coil and parallel to the conducting ribbons of the excitation coil which are shown in detail in FIG. 2b. In the embodiment shown in the drawings, the array is inserted in a slot 46 in the membrane as best seen in FIG. 3 which discloses an exemplary embodiment of the structural elements of the housing. The PC board edge along which the sensor array is mounted is adhesively bonded or otherwise affixed to the excitation coil at the midpoint to assure close contact of the array with the surface under investigation. Block 24 to which the PC board is mounted is urged downward by spring 28 reacting against the frame. Guide rods 29 are employed to retain the block and mounted array in a substantially tangential orientation with respect to the surface under investigation. The resilient elements of the frame are provided by the wheel bogeys 48 urging the wheels into intimate contact with the surface under inspection by springs 50 reacting against receivers on the frame. The membrane is mounted to the lower surface of the bogeys intermediate the wheels. The diameter of the wheels is predetermined to maintain the intimate contact of the membrane and the excitation coil mounted thereto with the surface undergoing inspection. The connectors for the array receive ribbon cables 52 for interconnection to a terminal connector 54 mounted on internal element 56 for further connection to an external power and data cable. Power for the excitation coil is provided through connector 58, which for the embodiment shown is attached to slider block 24 which acts as the array holder/fixture.

FIG. 4 further shows details of the exemplary embodiment. A position encoder 60 such as an encoder wheel, optical sensor or track ball is mounted from frame 34 intermediate the wheels and adjacent the excitation coil and membrane provides for continuous position registration. Manual operation of the sensing device is enhanced with a "mouse" like handle 62 mounted to the frame. Integral control buttons 64 and/or scroll wheel 66 provide for control of the sensor and operational functions of the complete unit as described in companion patent application Ser. No. 11/163,785 entitled Control for Hand-held Imaging Array Using A Computer Mouse Configuration having a common assignee with the present application, the disclosure of which is incorporated herein by reference as though fully set forth. A connecting ribbon cable 68 operably connects to terminal connector 54 of FIG. 3 for power and data communication between the sensor array and excitation coil and external electronics while an additional cable 70 provides connection to the control elements and position encoder.

The entire unit is ergonomically constructed, permitting easy hand scanning. As the unit is scanned in the direction indicated, the downward pressure exerted by the inspector keeps the flexible membrane mounted excitation coil in contact with the surface of the item being inspected. The MR array is maintained in contact with the surface via the spring which pushes down on the block to which the array PC board is mounted. The array is linearly oriented perpendicular to the plane of FIG. 1a and in the plane of FIG. 1b, with the sensors sensitive to the field in the direction normal to the surface of the item being inspected. As the unit is scanned over the surface, the field values are recorded, and their image is displayed on a computer monitor.

For the embodiment shown, the orientation and configuration of the scanning head created by the flexible membrane, coil and PC board mounted sensors is such that scanning in an axis directed along the circumference of the curved surface, the full sensor array is always seated such that it is in contact along its full length with the surface being inspected, being above that surface by the thickness of the excitation coil, which is very thin, and a thin insulating layer which may be created using mylar tape or similar material. The configuration shown in the FIG. 1a permits scanning for cracks that are parallel to the circumferential direction while the configuration shown in the FIG. 1b permits scanning for cracks that are perpendicular to the circumferential direction.

Similarly, the flexible membrane and coil remain intimately engaged with the surface under inspection for scan directed along an axis perpendicular to the circumference of the curved surface. In this orientation, as shown in FIG. 1(b), the MR array remains intimately engaged at the mid point. The array is shown in the drawings is exaggerated in size for clarity, being much larger than in actual practice. In an exemplary device embodying the inventions the array is one inch long, and therefore extends only one-half inch to each side of the center of the four-inch wide excitation coil. As can be seen from the drawing, the sensors that are farther from the center of the array are above the upper surface of the flexible excitation coil. This causes them to record a field reading which is slightly less than that which sensors located closer to the middle of the array experience. This discrepancy, although small for very deep inspections, requires compensation. In an alternative embodiment, the ribbons of the coil are oriented parallel to the direction of translation and the array is located perpendicular to the ribbons with the center of the array located at the geometric center of the coil. In addition, the field due to the excitation coil increases linearly with distance from the center of the coil for small distances, and therefore limits the excitation amplitude which also requires compensation.

Figure 5:
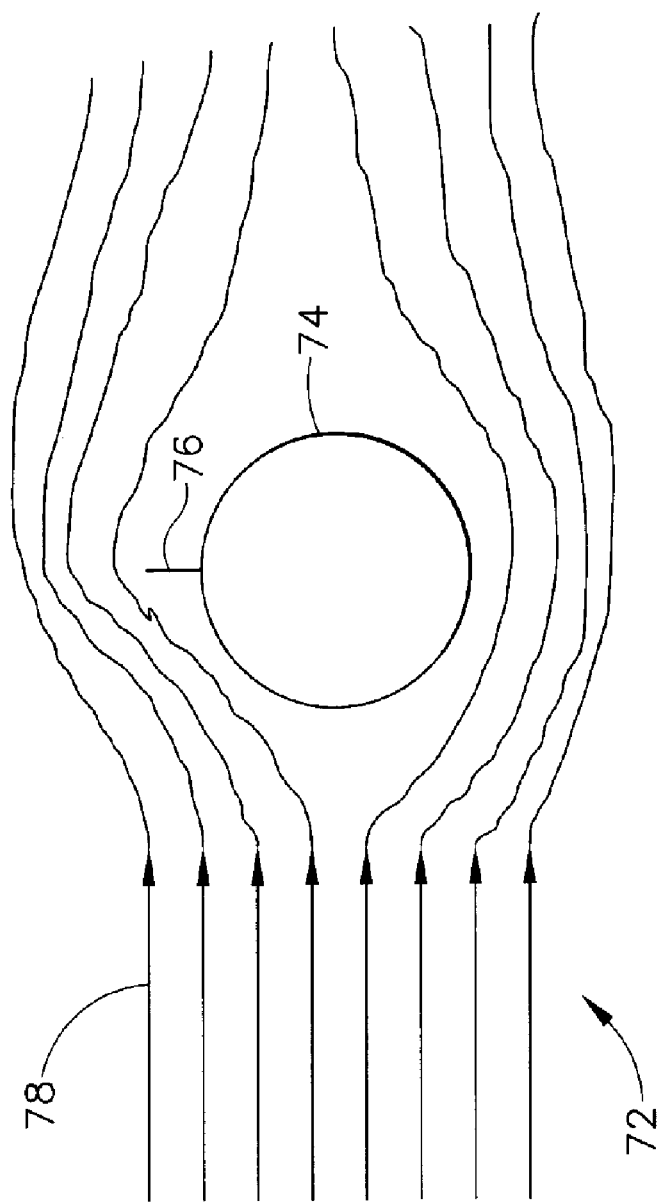
FIG. 5 is a side view representing unidirectional current "sheet" excitation.

Careful choice of the excitation frequency, the excitation amplitude, the bias strap current, and the detection phase permit detection of features significantly below what conventional eddy current techniques are capable of providing. The present invention precludes the requirement for a circular coil for excitation of eddy currents around a fastener through the use of a unidirectional current. This provides for rapid scanning along a line of fasteners as quickly as the excitation frequency, sensor drive electronics, and data collection hardware permit. It is only necessary to know in what direction cracks tend to propagate for a given inspection. This is virtually always the case for fatigue cracks. Regions of corrosion look like two dimensional cracks, so they pose no problem for the geometry of the present invention. The current is directed so that it intercepts the cracks. Rapid scanning then circumvents the difficulties and delays associated with the circular geometry. Scans are taken with a unidirectional current "sheet" as the excitation as shown in FIG. 5.

The sheet of current 72 coming in from the left is forced to bend around a hole 74, bunching it up at top and bottom, creating stronger field in those locations. The field will be pointing up at top center of the figure, and down at bottom center of the figure. In the presence of a flaw 76 the field lines 78 crowd together more at the top than at the bottom. This break in the symmetry provides the indication of the presence of the flaw.

Having now described the invention in detail as required by the patent statutes, those skilled in the art will recognize modifications and substitutions to the specific embodiments disclosed herein. Such modifications are within the scope and intent of the present invention as defined in the following claims.

What is claimed is:

1. A non-destructive testing device comprising:
   an excitation coil having a plurality of conductor ribbons attached to a flexible membrane;
   a frame supporting the membrane and incorporating means for translation across a curved surface to be inspected,
   resilient means for maintaining the membrane with the excitation coil and the translation means in intimate contact with the surface to be inspected; and,
   a magnetoresitive (MR) array supported within the frame proximate the membrane and surface wherein elements of the MR array are arranged in a line parallel to the excitation coil conductor ribbons.

2. A non-destructive testing device as defined in claim 1 further comprising means for measurement of translation of the MR array across the surface under inspection.

3. A non-destructive testing device as defined in claim 1 wherein the conductor ribbons are arranged perpendicular to the direction of translation and provide a unidirectional current sheet.

4. A non-destructive testing device as defined in claim 1 wherein the translation means comprises a plurality of wheels mounted to the frame.

5. A non-destructive testing device as defined in claim 1 wherein the MR array comprises a plurality of GMR sensors.

6. A non-destructive testing device as defined in claim 1 further comprising an ergonomic handle mounted to the frame for operative translation of the frame and having at least one control means for scanning of the surface under inspection.

7. A non-destructive testing device as defined in claim 5 wherein each sensor has its axis of sensitivity normal to the surface being scanned.

8. A non-destructive testing device as defined in claim 1 wherein translation across the surface is accomplished in a direction substantially parallel to a circumference of the curved surface being inspected.

9. A non-destructive testing device as defined in claim 1 wherein translation across the surface is accomplished in a direction substantially perpendicular to a circumference of the curved surface being inspected.

10. A non-destructive testing device comprising:
    an excitation coil having a plurality of conductor ribbons attached to a flexible membrane;
    a frame supporting the membrane and incorporating means for translation across a curved surface to be inspected,
    resilient means for maintaining the membrane with the excitation coil and the translation means in intimate contact with the surface to be inspected; and,
    a magnetoresitive (MR) array supported within the frame proximate the membrane and surface wherein the MR array is inserted into a slot in the membrane.

11. A method for non-destructive testing comprising the steps of:
    providing a frame supporting an excitation coil having a plurality of conductor ribbons attached to a flexible membrane and a magnetoresitive (MR) array supported within the frame proximate the membrane and surface and arranged in a line parallel to the excitation coil conductor ribbons;
    translating the frame across a curved surface to be inspected; and
    resiliently maintaining the membrane with the excitation coil and the translation means in intimate contact with the surface to be inspected.

12. A non-destructive testing method as defined in claim 11 further comprising the step of measuring the translation of the MR array across the surface under inspection.

13. A non-destructive testing method as defined in claim 11 wherein the step of providing includes arranging the conductor ribbons perpendicular to the direction of translation.

14. A non-destructive testing method as defined in claim 11 wherein the step of arranging the MR array elements includes mounting each sensor with its axis of sensitivity normal to the surface being scanned.

15. A non-destructive testing method as defined in claim 11 wherein the step of translating across the surface is accomplished in a direction substantially parallel to a circumference of the curved surface being inspected.

16. A non-destructive testing method as defined in claim 11 wherein the step of translating across the surface is accomplished in a direction substantially perpendicular to a circumference of the curved surface being inspected.

17. A method for non-destructive testing comprising the steps of:
provide a frame supporting an excitation coil having a plurality of conductor ribbons attached to a flexible membrane and a magnetoresitive (MR) array supported within the frame proximate the membrane and surface, the MR array inserted into a slot in the membrane;
translating the frame across a curved surface to be inspected; and
resiliently maintaining the membrane with the excitation coil and the translation means in intimate contact with the surface to be inspected.

* * * * *